US012324601B2

(12) United States Patent
Yang et al.

(10) Patent No.: US 12,324,601 B2
(45) Date of Patent: Jun. 10, 2025

(54) INTERATRIAL SEPTOPLASTY CUTTING DEVICE

(71) Applicant: Medtronic, Inc., Minneapolis, MN (US)

(72) Inventors: Zhongping Yang, Woodbury, MN (US); Lars M. Mattison, Blaine, MN (US); Jorge A. Vergen, Woodbury, MN (US); Devan D. Barth, Ramsey, MN (US); Noah A. Deraney, Chanhassen, MN (US); Christine R. Huyett, Arden Hills, MN (US); Clayton P. Witherspoon, Eden Prairie, MN (US); Jia Yuan Neoh, Minneapolis, MN (US); Lina T. Abajebel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 309 days.

(21) Appl. No.: 17/934,018

(22) Filed: Sep. 21, 2022

(65) Prior Publication Data

US 2023/0115101 A1 Apr. 13, 2023

Related U.S. Application Data

(60) Provisional application No. 63/254,247, filed on Oct. 11, 2021.

(51) Int. Cl.
*A61B 17/32* (2006.01)
*A61B 17/34* (2006.01)
*A61B 17/00* (2006.01)

(52) U.S. Cl.
CPC ............. *A61B 17/32* (2013.01); *A61B 17/34* (2013.01); *A61B 2017/00336* (2013.01); *A61B 2017/00743* (2013.01)

(58) Field of Classification Search
CPC ............... A61B 17/32; A61B 17/34; A61B 2017/00336; A61B 2017/00743;
(Continued)

(56) References Cited

U.S. PATENT DOCUMENTS 5,196,024 A * 3/1993 Barath ........... A61B 17/320725
606/191
5,697,944 A * 12/1997 Lary ................. A61B 17/3209
606/159
(Continued)

FOREIGN PATENT DOCUMENTS

WO 2021011502 A1 1/2021

OTHER PUBLICATIONS

International Search Report and Written Opinion of International Application No. PCT/IB2022/059132 dated Nov. 21, 2022, 8 pp.
(Continued)

*Primary Examiner* — Julian W Woo
(74) *Attorney, Agent, or Firm* — Shumaker & Sieffert, P.A.

(57) ABSTRACT

A medical device having an elongate body with a proximal portion, a distal portion, and defining a lumen therethrough. The medical device has an expandable element coupled to the distal portion of the elongate body, the expandable element defining a proximal portion, a distal portion opposite the proximal portion and an intermediate portion disposed between the proximal portion and the distal portion. The expandable element also has an inner surface and an outer surface opposite the inner surface. The medical device has a plurality of cutting members, each cutting member being coupled with the outer surface of the expandable element, each cutting member having a proximal end and a distal end opposite the proximal end, the proximal end being proximate the proximal portion of the expandable element
(Continued)

and the distal end being proximate to the intermediate portion of the expandable element.

19 Claims, 9 Drawing Sheets

(58) Field of Classification Search
CPC ...... A61B 17/320725; A61B 17/32075; A61B 17/320016
USPC ...................................... 604/103.08; 606/169
See application file for complete search history.

(56) References Cited

U.S. PATENT DOCUMENTS

| | | | |
|---|---|---|---|
| 6,632,231 B2 * | 10/2003 | Radisch, Jr. ... | A61B 17/320725 606/159 |
| 6,951,566 B2 * | 10/2005 | Lary .............. | A61B 17/320725 606/159 |
| 10,143,838 B2 | 12/2018 | Grubac et al. | |
| 10,292,690 B2 | 5/2019 | Celermajer et al. | |
| 10,898,707 B2 | 1/2021 | Eggen et al. | |
| 11,883,061 B2 * | 1/2024 | Gunderson .... | A61B 17/320725 |
| 2006/0111736 A1 * | 5/2006 | Kelley .......... | A61B 17/320725 606/159 |
| 2012/0191111 A1 * | 7/2012 | Aggerholm .... | A61B 17/320725 606/159 |
| 2014/0142564 A1 | 5/2014 | Werneth et al. | |
| 2015/0182282 A1 | 7/2015 | Zemel et al. | |
| 2017/0113035 A1 | 4/2017 | Bonner et al. | |
| 2018/0056051 A1 | 3/2018 | Kabra | |
| 2018/0177516 A1 | 6/2018 | Vardi et al. | |
| 2020/0315652 A1 | 10/2020 | Vetter et al. | |
| 2021/0315629 A1 | 10/2021 | Yang et al. | |
| 2021/0369321 A1 | 12/2021 | Yang et al. | |
| 2022/0370120 A1 | 11/2022 | Yang et al. | |

OTHER PUBLICATIONS

National Heart, Lung, and Blood Institute (NHLBI), "Basilica Procedure", Facebook, Jun. 17, 2019, 2 pp., https://fb.watch/fr4FRHXgVw/.

* cited by examiner (A)

(B)

(C)

INTERATRIAL SEPTOPLASTY CUTTING DEVICE

This application claims the benefit of U.S. Provisional Application Ser. No. 63/254,247, filed Oct. 11, 2021, the entire content of which is incorporated herein by reference.

FIELD

The present technology is generally related to a medical device having at least one cutting element and method for using the medical device with the cutting element within a patient's heart.

BACKGROUND

Cardiovascular diseases are some of the most common causes of death in the world. Heart failure is one significant cardiovascular disease that is generally known to decrease the heart's ability to pump and/or fill with blood. The number of people diagnosed with heart failure is constantly increasing due to a variety of different issues. In part, this increase may be attributed to more people surviving heart attacks due to scientific advances and then those individuals face a higher heart failure risk afterward. Also, other health issues are likely major contributors to this rise in the number of people experiencing heart failure. For example, people with diabetes and those that are obese are at greater risk for developing heart failure.

Elevated pressure within the left atrium of the heart is a known contributor to heart failure and other heart related diseases. Having an elevated pressure within the left atrium can increase the size of the left atrium which has been identified as a precursor of atrial fibrillation, stroke one atrial fibrillation is present, and heart failure.

Health conditions associated with heart failure and left atrial enlargement can cause life altering symptoms or may not be discovered until testing is performed related to other medical issues. Individuals with heart failure may experience a variety of different symptoms that may impact their day to day living including, but not limited to, breathlessness or shortness of breath, fatigue, rapid or irregular heartbeats, lack of appetite or nausea, dizziness, swelling, weight gain, chest pain and fainting.

There are limited treatments available to treat a patient with elevated pressures within the left atrium of the heart. While there are preventative steps that can be taken to try and lower the risks associated with elevated pressures within the left atrium, these do not cure the problem. For example, eating a healthy diet, exercising regularly, losing weight if overweight, practicing stress management, and managing blood pressure and cholesterol can try and lessen the effects of these cardiovascular issues. Some of the available treatments include mediations, surgery to repair any damaged valves, as well as certain medical devices that may be implanted to help the heart continue to function. Ultimately, there are limited therapies that are available to treat and manage heart failure and elevated pressure within the left atrium of the heart.

SUMMARY

The techniques of this disclosure generally relate to a medical device having at least one cutting element and method for using the medical device with the cutting element within a patient's heart. In one aspect, the present disclosure provides a medical device having an elongate body with a proximal portion, a distal portion, and defining a lumen therethrough; an expandable element coupled to the distal portion of the elongate body, the expandable element defining a proximal portion, a distal portion opposite the proximal portion and an intermediate portion disposed between the proximal portion and the distal portion, the expandable element having an inner surface and an outer surface opposite the inner surface; and a plurality of cutting members, each cutting member being coupled with the outer surface of the expandable element, each cutting member having a proximal end and a distal end opposite the proximal end, the proximal end being proximate the proximal portion of the expandable element and the distal end being proximate to the intermediate portion of the expandable element.

In another aspect of this embodiment, the expandable element is a conical shaped balloon.

In another aspect of this embodiment, each cutting member further includes a plurality of segmented portions, each segmented portion of the plurality of segmented portions being separated from an adjacent segmented portion by a slot.

In another aspect of this embodiment, each segmented portion from the plurality of segmented portions includes a cutting element.

In another aspect of this embodiment, each cutting member has three segmented portions and two slots, each segmented portion being separated from the adjacent segmented portion by one slot.

In another aspect of this embodiment, the plurality of cutting members comprises four cutting elements.

In another aspect of this embodiment, each cutting member of the four cutting members comprises three segmented portion, each segmented portion having a cutting element.

In another aspect of this embodiment, each cutting element extends distally away from the outer surface of the expandable element.

In another aspect of this embodiment, the medical device further comprises a sheath, the expandable element being transitional between a retracted configuration and an expanded configuration, when the expandable element is in the retracted configuration, the sheath is disposed over at least a portion of the expandable element.

In another aspect of this embodiment, when the expandable element is in the expanded configuration, the sheath is not disclosed over the expandable element.

In another aspect of this embodiment, the expandable element is a conical balloon, the proximal portion having a first diameter, the distal portion have a second diameter, and the intermediate portion having a third diameter, the third diameter being larger than the first diameter and the second diameter.

In another aspect of this embodiment, the first diameter is the same as the second diameter.

In another embodiment, the medical device has an elongate body having a proximal portion, a distal portion, and defining a lumen therethrough; a balloon being coupled to the distal portion of the elongate body, the balloon having a conical shape and defining a proximal portion, a distal portion opposite the proximal portion and an intermediate portion disposed between the proximal portion and the distal portion, the balloon having an inner surface and an outer surface opposite the inner surface; a plurality of cutting members, each cutting member being coupled with the outer surface of the balloon, each cutting member having a proximal end and a distal end opposite the proximal end, the proximal end being proximate the proximal portion of the balloon and the distal end being proximate to the intermediate portion of the balloon; and In another aspect of this embodiment, a plurality of segmented portions defined between the proximal end and the distal end of the cutting members, each segmented portion being separated from an adjacent segmented portion by a slot.

In another aspect of this embodiment, each segmented portion from the plurality of segmented portions includes at least one cutting element.

In another aspect of this embodiment, each cutting member has three segmented portions and two slots, each segmented portion being separated from the adjacent segmented portion by one slot.

In another aspect of this embodiment, the plurality of cutting members comprises four cutting elements.

In another aspect of this embodiment, each cutting member of the four cutting members comprises three segmented portion, each segmented portion having a cutting element.

In another embodiment, a method for delivering a medical device, comprising: positioning a medical device proximate the fossa ovalis of a patient's heart in the right atrium, the medical device including: an elongate body having a proximal portion, a distal portion, and defining a lumen therethrough; an expandable element being coupled to the distal portion of the elongate body, the expandable element defining a proximal portion, a distal portion opposite the proximal portion and an intermediate portion disposed between the proximal portion and the distal portion, the expandable element having an inner surface and an outer surface opposite the inner surface; and a plurality of cutting members, each cutting member being coupled with the outer surface of the expandable element, each cutting member having a proximal end and a distal end opposite the proximal end, the proximal end being proximate the proximal portion of the expandable element and the distal end being proximate to the intermediate portion of the expandable element; advancing a traumatic device through the lumen of the medical device; puncturing the fossa ovalis with the traumatic device to create an orifice; withdrawing the traumatic device through the lumen; advancing the medical device through the orifice from the right atrium of the heart to the left atrium of the heart until the distal portion of the medical device is in the left atrium; transitioning the distal portion of the medical device into an expanded configuration; retracting the distal portion of the medical device in the expanded configuration from the left atrium to the right atrium of the heart; transitioning the distal portion from the expanded configuration to a retracted configuration; and withdrawing the medical device from the body.

In another aspect of this embodiment, the traumatic device a puncturing device or a guidewire.

In another aspect of this embodiment, the plurality of cutting members are four cutting members.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
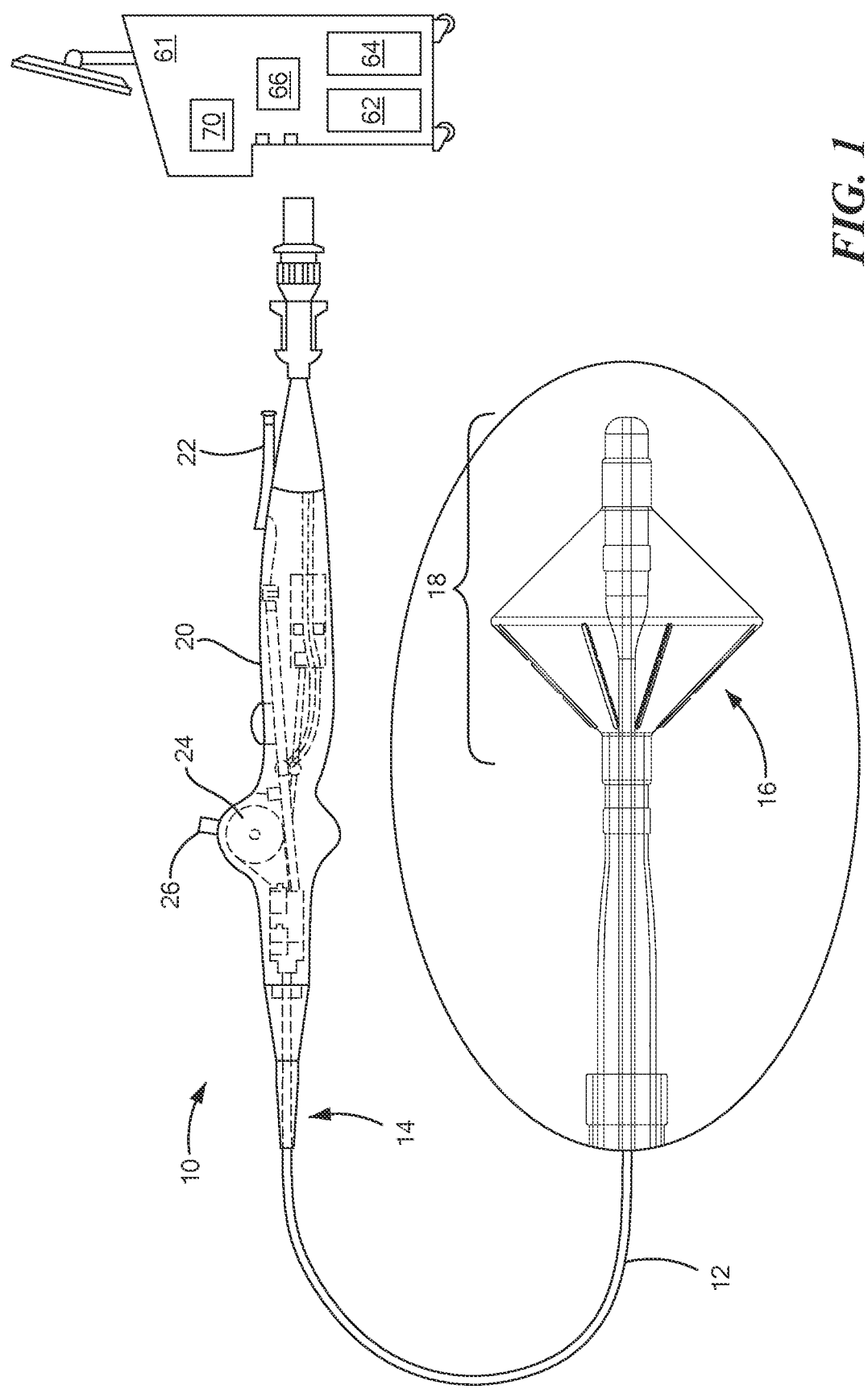
FIG. 1 is a perspective view of a medical device constructed in accordance with an embodiment of the present invention.

Before describing in detail exemplary embodiments, it is noted that the embodiments reside primarily in combinations of device and system components related to a medical device. Accordingly, the device and system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Referring now to the drawings in which like reference designators refer to like elements, there is shown in FIG. 1 an exemplary medical device constructed in accordance with the principles of the present application and designated generally as 10. The medical device 10, according to one embodiment of the disclosure, may be configured to be maneuvered through a patient's vascular system, or another portion of a patient's body. As a non-limiting example, the medical device 10 may be navigated into the left atrium of the heart through the femoral vein and then into the right atrium of the heart via the interior vena cava. Once the medical device 10 is navigated into the right atrium of the heart, the medical device 10 may be inserted into the left atrium of the heart via a transseptal puncture. Once the medical device 10 is in the left atrium, the medical device 10 may be used to puncture through the atrial septum from the left atrium of the heart into the right atrium of the heart, such as through the area of septal tissue known as the fossa ovalis. The medical device 10 may also be maneuvered through other areas of the body as well.

With reference to FIG. 1, the medical device 10 may generally define an elongated and flexible catheter body 12 with a proximal end 14 and a distal end 16 having a distal portion 18 as well as a handle 20 at the proximal end 14 of the catheter body 12. The catheter of the present invention may be sized and dimensioned for intraluminal and transseptal access to a patient's heart. The catheter body 12 may be formed and dimensioned to provide sufficient column and torsional strength to support standard interventional procedures such as those which access the vasculature from a femoral vein or artery and further access the patient's heart. The catheter shaft may include reinforcement elements or otherwise be constructed to provide desired degrees of stiffness, flexibility, and torque transmission along the length of the body and at selected locations along its length. The catheter body 12 may have portions or components of differing size, thickness or flexibility, and may include wires, braiding, changes in wall thickness, additional wall layers or catheter body 12 components, sleeves, or other components reinforcing or otherwise supplementing an outer wall or thickness along its length. Some portions that may experience significant loading or torque during a particular procedure may also include reinforcement. For example, the catheter body 12 may be a braided prebax shaft with different durometer segments to create the desired curve within the catheter body 12 depending upon where and how the medical device 10 is going to be maneuvered in the body. The braiding of the prebax shaft may provide resistance and torque to the catheter body 12.

FIG. 1 depicts a medical device 10 with a distal portion 18 and a handle 20. The handle 20 may include one port 22 or more than one port 22. As a non-limiting example, the one port 22 may be configured to receive a device which may include a puncturing device and/or a guidewire. In one example, the catheter body 12 may be sized to receive the puncturing device, the guidewire, and/or any other medical device that may be inserted into the port 22. Additionally, a different port 22 or the same port 22 may be configured to receive an inflation and deflation lumen as well as other devices that may be used with the medical device 10. The handle 20 may also have additional ports 22 and is not limited to one or two ports 22 and the port 22 may be configured to receive a variety of different devices depending upon how and where the medical device 10 is being used.

The handle 20 may further include an actuator 24 in communication with a deflection element (not shown) configured to move at least a portion of the catheter body 12 in any direction. As a non-limiting example, the deflection element may be a wire configured to fit within the catheter body 12. The wire within the catheter body 12 may extend to the distal portion 18 or anywhere within the catheter body 12. The actuator 24 may have a moveable component 26 configured to move the deflection element in a particular direction. When the moveable component 26 on the actuator 24 is moved in a particular direction, a portion of the catheter body 12, including the distal portion 18, can move to the left, right, and/or up or down. For example, the movable component 26 may be a bar which is attached to the actuator 24 that can be moved up and down, the upwards movement of the bar moves the deflection element upwards and the downwards movement of the bar moves the deflection element downwards. If the movable component 26 includes a button, depressing the button moves the deflection element to the left and lifting the button upwards moves the deflection element to the right. Other movable components 26 may be used to move a portion of the catheter body 12 in any direction. Also, the movable component 26 may be pushed down which may have a locking mechanism so that the deflection element cannot be moved or the movable component 26 may be lifted up which may release the locking mechanism so that the deflection element can be freely movable.

Figure 2:
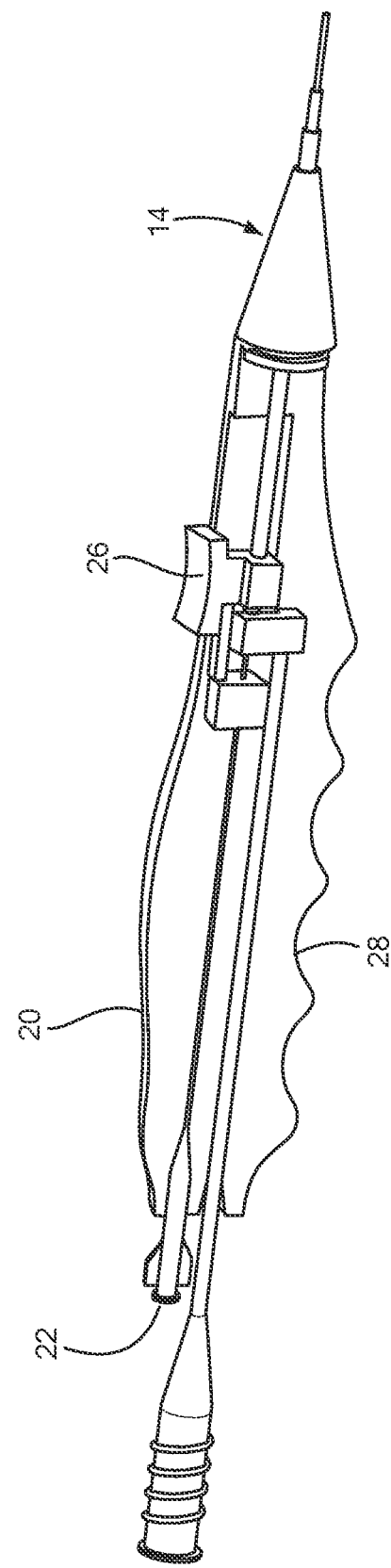
FIG. 2 is a perspective view of an exemplary handle constructed in accordance with an embodiment of the present invention.

One configuration of the handle 20 of the medical device 10 is shown in FIG. 2. The handle 20 may be coupled to the proximal end 14 of the catheter body 12. The handle 20 may include one or more steering or deflection components for manipulating the catheter body 12, the distal portion 18 of the medical device 10, and/or any additional components of the medical device 10. In the embodiment of the handle shown in FIG. 2, the handle 20 has a gripping element 28 which gives the user of the medical device a more secure way to hold the handle 20 in one hand while also being able to move the movable component 26 of the actuator 24 in a variety of different directions. For example, the gripping element 28 may be part of the handle 20 to allow the user of the medical device 10 to provide a more secure way to wrap the hand around the handle 20 and the gripping element 28 may be releasably or permanently secured to the handle 20. As shown in FIG. 2, the gripping element 28 is integrated within the body of the handle 20 but the gripping element 28 may be releasably secured to the handle 20 so that a customized gripping element 28 may be used with the handle 20. The gripping element 28 may be ergonomically profiled on one portion of the handle 20 so that it conforms to the user's hand shape. Additionally, the griping element 28 may have friction-increasing material to help with stability when using the medical device 10 with one or two hands. The friction increasing material may include an elastic rubber material, a coating, a friction increasing strip or another material that may increase the friction between the hand of the user and the gripping element 28 of the handle 20.

Figure 3:
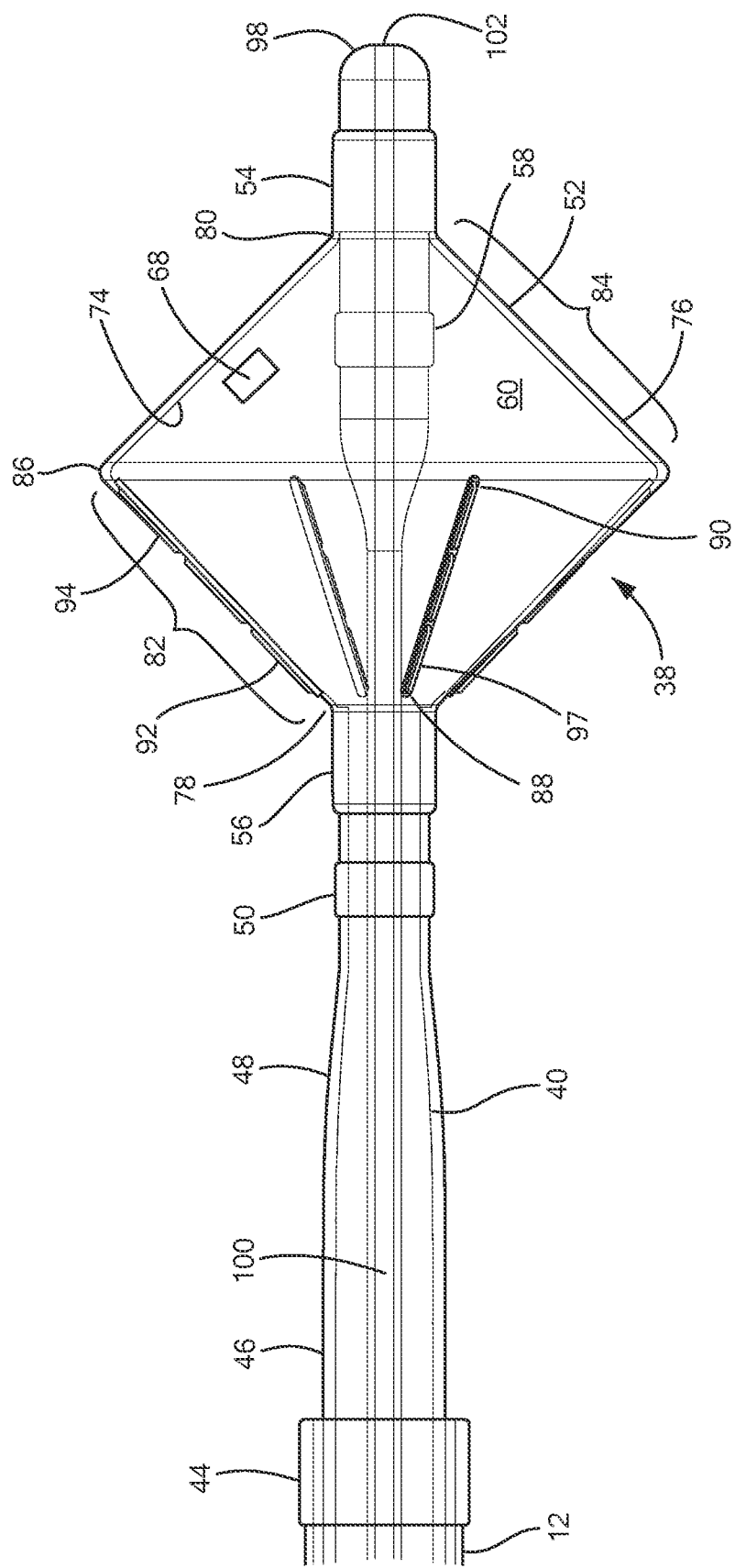
FIG. 3 is a perspective view of the distal portion from the medical device in FIG. 1 in an expanded configuration.
Figure 4:
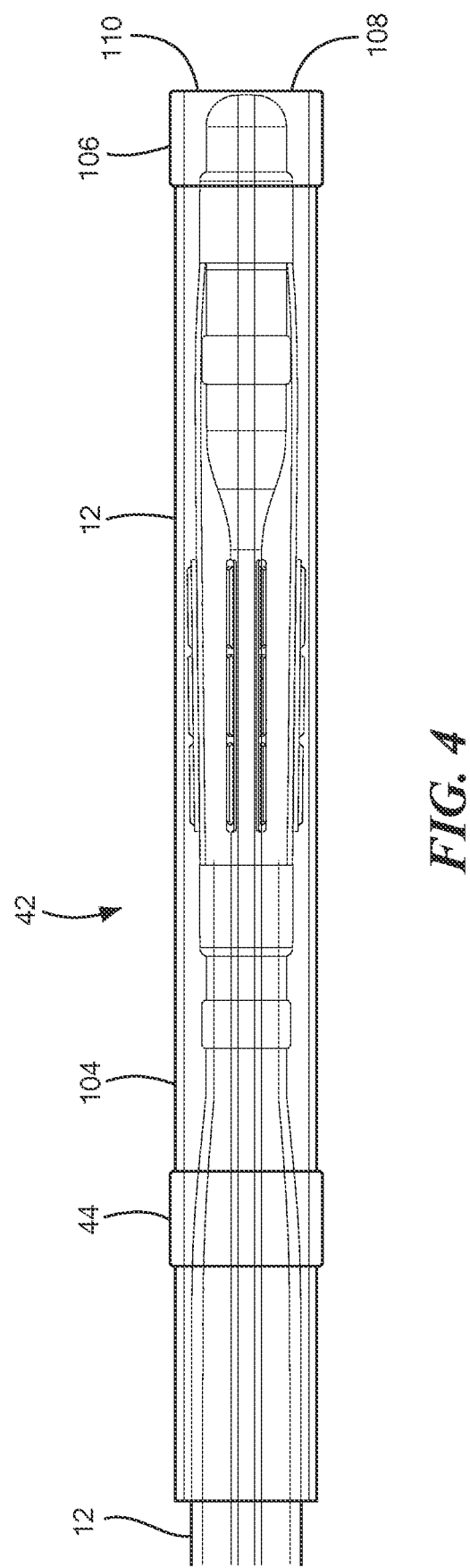
FIG. 4 is a perspective view of the distal portion from the medical device in FIG. 1 in a retracted configuration.

One configuration of the distal portion 18 of the medical device 10 is shown in FIG. 3. In the configuration of the distal portion 18 as shown in FIG. 3, the distal portion is in an expanded configuration 38. The distal portion 18 may include an elongate body 40 and the elongate body 40 may be sized to be received within the catheter body 12. Having the elongate body 40 sized to be received within the catheter body 12 allows the distal portion 18 to be received within the catheter body 12 such that the distal portion 18 may be fully retracted within the catheter body 12 to allow for the medical device 10 to maneuver through the vessels of the body in a retracted configuration 42 as shown in FIG. 4 until the distal portion 18 of the medical device 10 is proximate the fossa ovalis portion of the heart. Once the distal portion 18 is proximate the fossa ovalis, the distal portion 18 may be transitioned from the retracted configuration 42 into the expanded configuration 38. The catheter body 12 may include an end piece 44 on the distal end 16 of the catheter body 12. The end piece 44 may be a variety of different shapes and sizes to give additional support to the distal end 16 of the catheter body 12 so that when the distal portion 18 is being expanded and retracted from the catheter body 12, the catheter body 12 does not collapse on the distal portion 18 and the distal portion 18 can be freely movable within and outside of the catheter body. The end piece 44 may also provide additional support as the device is inserted through the septal wall and the end piece 44 may be sized and shaped so that when the medical device 10 is moved through the septal wall from the right atrium to the left atrium and from the left atrium to the right atrium that the end piece 44 does not enter and/or go through the septal wall. Accordingly, when the medical device 10 is moved to the left and right atrium of the heart, the end piece 44 will not enter into the left atrium of the heart as it will not move past the septal wall. Additionally, when the medical device 10 is moved from the right atrium into the left atrium of the heart, the end piece 44 may be connected with the actuator 24 such that movement of the actuator 24 may release tension on the distal portion 18 of the medical device 10 so that the distal portion 18 of the medical device 10 may be expanded.

Continuing to refer to FIG. 3, the elongate body 40 may be all the same circumference or the elongate body 40 may have a circumference that tapers in a proximal to distal direction. As shown in FIG. 3, the elongate body 40 has a proximal portion 46 and a distal portion 48. The proximal portion 46 of the elongate body 40 has a diameter that is larger than the diameter of the distal portion 48 of the elongate body 40. The elongate body 40 may also have a proximal portion 46 that has a smaller diameter than the diameter of the distal portion 18. The elongate body 40 may have different sizes and shapes so that when the distal portion 18 is in the retracted configuration 42, all of the various components of the distal portion 18 may be received within the catheter body 12 without any obstructions. The elongate body 40 my optionally include a removable component 50. The removable component 50 may be secured to a portion of the elongate body 40 including the distal portion 48 of the elongate body 40. Additionally or alternatively, the removable component 50 may be secured to the proximal portion 46 of the elongate body 40 or any other portion of the elongate body 40. The removable component 50 may be a marker band that can be used to help with placement and guidance of the medical device 10 during a medical procedure. For example, the marker may be used to provide high levels of visibility under an x-ray fluoroscope to allow a medical provider to precisely locate the medical device 10 deep within the tissue of the body so that the medical device 10 can be properly placed within the body. For example, the removable component 50 may be used to see when the medical device 10 is near the septal wall of the heart in the patient. The distal portion 18 may further include an expandable element 52 and the expandable element 52 may be a balloon that can be expanded into a variety of different shapes. In one exemplary embodiment, the expandable element 52 may be expanded to be in the shape of a conical balloon.

In the embodiment shown in FIG. 3, the expandable element 52, such as a cryoballoon, has a distal neck 54 that is coupled to the elongate body 40 and a proximal neck 56 that is also coupled to the elongate body 40. The proximal 56 and distal 54 necks of the expandable element 52 may be coupled to the elongate body 40 respectively, using any suitable means, such as with adhesives, chemical bonding, laser welding, with one or more mechanical coupling elements, or the like. The distal neck 54 may help in holding the expandable element 52 in place so that the expandable element 52 does not move beyond the distal neck 54 in a more distal direction on the medical device 10. The proximal neck 56 may also help in holding the expandable element 52 in place so that the expandable element 52 does not move beyond the proximal neck 56 in a more proximal direction on the medical device 10. The proximal neck 56 may also help to seal the expandable element 52 from leaks including the leaking of any solids, liquids, or gasses from within the expandable element 52. Further, the expandable element 52 may be a compliant or highly compliant balloon composed of one or more materials such as polyurethane, polyolefin copolymer (POC), or other material that allows the balloon to be "soft" (that is, easily deformable and/or conformable to an area of targeted tissue) when fully inflated.

The medical device 10 may further include one or more nozzles, orifices, or other delivery elements 58 for delivering fluid or air to the interior chamber 60 of the expandable element 52. During operation, a gas or a liquid may flow from a unit 61, and the unit may have a variety of different components, including a supply reservoir 62 where the gas or liquid may flow through a delivery conduit (not shown) in the catheter body 12 to the distal portion 18, where the liquid or gas may then enter in interior chamber 60 of the expandable element 52, such as through one or more delivery elements 58, where the liquid or gas may enter and expand the expandable element 52. Once the liquid or gas is no longer needed in the interior chamber 60 of the expandable element 52, the liquid or gas may then pass from the interior chamber 60 of the expandable element 52 to a recovery reservoir 64 and/or scavenging system through a fluid return conduit within the catheter body 12. Further, the size of the expandable element 52 when fully inflated may be chosen by the user based on various factors such as the patient's anatomy and vessel diameter. The medical device 10 may further include one or more flow control valves in fluid flow pathways of the medical device 10 and a vacuum pump or vacuum source 66 to remove liquid or gas from the interior chamber 60 of the expandable element 52.

In one embodiment, the medical device 10 and/or the unit 61 may include one or more sensors. For example, the expandable element 52 may include on or more pressure sensors 68 on and/or within the expandable element 52. These pressure sensors 68 may be configured to record pressure waves from or through the expandable element 52. Additionally or alternatively, one or more sensors may be used to evaluate inflation and/or configuration of the expandable element 52. For example, in one embodiment, the unit 61 may include a pressure sensor 70 that is in fluid communication with the expandable element 52.

The expandable element 52 may further include a plurality of cutting members 72, and each cutting member from the plurality of cutting members 72 may be coupled with the expandable element 52. The expandable element 52 may have an interior surface 74 which is within the interior chamber 60 of the expandable element 52 as well as an exterior surface 76 which is directly opposite the interior surface 74. Each of the cutting members 72 may be coupled with the interior surface 74 and/or the exterior surface 76 of the expandable element 52. For example, the cutting members 72 me be secured to the expandable element 52 with a polymer, for example a polymeric adhesive may be used to secure the cutting members 72 to the expandable element 52. Alternatively, a connecting member (not shown) may be secured to the expandable element 52 and the cutting members 72 may be secured to the connecting member. As shown in FIG. 2, each cutting member 72 is coupled to the exterior surface 76 of the expandable element 52. The expandable element 52 may also include a proximal end 78 and a distal end 80 that is opposite the proximal end 78. The expandable element may also include a proximal portion 82 which may be disposed proximate the proximal end 78 and a distal portion 84 of the expandable element 52 which may be disposed proximate the distal end 80. The expandable element 52 may further include an intermediate portion disposed between the proximal portion 82 and the distal portion 84. As shown in FIG. 2, the visible portion of the proximal portion 82 and the visible portion of the distal portion 84 each individually form a triangle. It will be understood that FIG. 2 only has a portion of the expandable element 52 visible and that the entirety of the expandable element surrounds the elongate body 40. When the expandable element 52 is in expanded, the expandable element 52 may have a conical shape. It will be understood that the expandable element 52 may have a variety of different shapes and may be inflated to a variety of different pressures depending upon the anatomy of the particular individual and what is being cut with the plurality of cutting members 72.

Each cutting member from the plurality of cutting members 72 may have a proximal end 88 and a distal end 90 that is opposite the proximal end 88. The proximal end 88 of the cutting member 72 may be disposed proximate to the proximal portion 82 of the expandable element 52. The distal end 90 of the cutting member 72 may be disposed proximate to the intermediate portion 86 of the expandable element 52. Each cutting member 72 may be disposed only on the proximal portion 82 of the expandable element 52. Alternatively, the cutting members 72 may be disposed anywhere on the expandable element 52 including anywhere on the exterior surface 76 as well as the interior surface 74 of the expandable element 52. Each cutting member 72 may also include at least one segmented portion 92. It will be understood that the at least one segmented portion 92 may include one segmented portion 92 or many segmented portions 92. In one exemplary embodiment, there may be three segmented portions 92 and each segmented portion 92 may be separated by a slot 94. There may be one slot 94 or a plurality of slots 94 on the cutting member 72. The segmented portions 92 may be disposed between the proximal end 88 of the cutting member 72 and the distal end 90 of the cutting member 72 and each slot 94 may be disposed between each segmented portion 92. Each segmented portion 92 may be separated from any adjacent segmented portion 92 by the slot 94. Each segmented portion 92 may further include at least one cutting element 96 and the at least one cutting element 96 may be any kind of cutting element 96 including a blade and each blade may be sharp enough to cut tissue within the body. The cutting members 72 and all the components of the cutting members 72 may be flexible so that when the expandable element 52 is expanding and contracting the cutting members 72 may be movable with the expansion and contraction of the expandable element 52. Each cutting element 96 may extend away from the exterior surface 76 of the expandable element 52 so that when exterior surface 76 of the expandable element 52 comes into contact with tissue in the body, the cutting element 96 may also come into contact with the tissue and cut the tissue.

When the expandable element 52 is expanded, in one configuration as shown in FIG. 2, each of the cutting members 72 may be arranged in a cruciform configuration 97 such that there are four cutting members 72 disposed around the expandable element 52. The set of four cutting members 71 are generally arranged in the shape of a cross when the expandable element 52 is in the expanded configuration 38 and the expandable element 52 is inflated.

The distal portion 18 may further include a distal end 98 and at least one lumen 100. In one embodiment, the distal end 98 may be extendable and retractable and in a proximal to distal and distal to proximal direction. For example, the movement of the distal end 98 may be activated by the movable component 26. Movement of the moveable component 26 in one direction may move the distal end 98 in a proximal direction and movement of the moveable component 26 in a second direction may move the distal end 98 in the distal direction. The moveable component 26 may be locked in place such that the distal end 98 is locked in any particular location. The at least one lumen 100 may be one lumen or more than one lumen and the lumen may be in communication with the handle 20 including the port 22 and the at least one lumen 100 may be an inflation lumen, a deflation lumen, and a lumen that is sized to receive other devices that may be used with the medical device 10. For example, the catheter body 12 may be sized to receive the puncturing device, the guidewire, and/or any other medical device that may be inserted into the port 22 or anywhere into the lumen 100. The puncturing device, guidewire, and/or any other medical device may be maneuvered through the catheter body 12 through the lumen 100 and into the distal portion 18 of the medical device 10 through the lumen 100. The lumen 100 may extend through the distal end 98 and the distal end 98 may include an aperture 102 where the lumen 100 terminates so that the puncturing device, the guidewire, and/or any other medical device may be extended distally from the distal end 98 so that the puncturing device, the guidewire, and/or any other medical device will come into contact with tissue that is disposed near the distal end 98 of the medical device 10.

Now referring to FIG. 4, the distal portion 18 of the medical device 10 is collapsed within a sheath 104 in the retracted configuration 42. The sheath 104 may be movable along the catheter body 12 and the sheath 104 may be collapsible, for example, within the end piece 44. When the sheath 104 is not over the distal portion 18, the sheath 104 may be disposed inside the end piece 44 so that the sheath 104 does not cause any obstruction when the medical device 10 is being moved within the vasculature of the patient. The end piece 44 may also be movable along the catheter body 12 or it may be secured to a portion of the catheter body 12 or anywhere else on the medical device 10. The sheath 104 may have a distal portion 106 and the distalmost portion of the distal portion 106 may be the distal end 108 of the sheath 104. At the distal end 108 of the sheath there may be an aperture 110 that is sized to receive the distal portion 18 of the medical device 10. Additionally, if for example, the puncturing device, guidewire, and/or any other medical device is maneuvered through the catheter body 12 through the lumen 100, the puncturing device, guidewire, and/or any other medical device may exit the sheath through the aperture 110 when in the retracted configuration 42. The sheath 104 when it is covering the distal portion 18 of the medical device 10 may be hallow so that the distal portion 18 of the medical device 10 may be fully received within the sheath 104 when in the retracted configuration 42.

Figure 5:
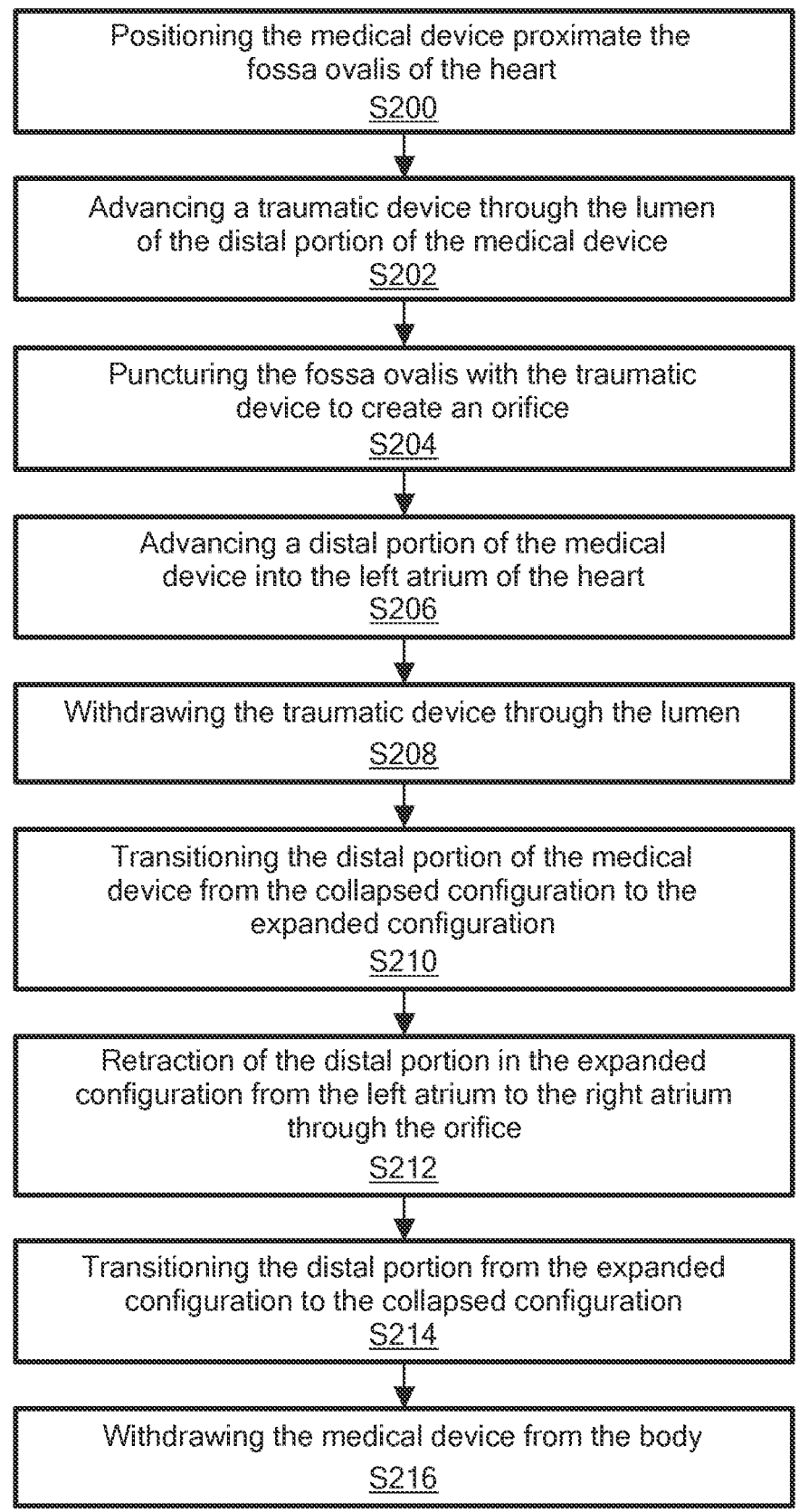
FIG. 5 is a method for using the medical device.

Now referring to FIG. 5, the medical device may be positioned in the fossa ovalis if the heart. S200. The medical device 10 may be in the retracted configuration 42 and maneuvered through the vasculature of the body in this retracted configuration 42 and put into a position proximate the fossa ovalis of the heart. A traumatic device 112, such as the puncturing device or guidewire, may be advanced through the lumen 100 of the distal portion 18 of the medical device 10 while the proximate portion 17 is in the retracted configuration 42. S202. The traumatic device 112 may be used to puncture the fossa ovalis to create an orifice 114.

S204. Once the traumatic device 112 has created the orifice 114, the distal portion 18 of the medical device may be advanced from the right atrium of the heart into the left atrium of the heart. S208. The traumatic device 112 may initially provide access from the right atrium of the heart into the left atrium of the heart by puncturing certain tissue and the traumatic device 112 may be used to maintain access to the left atrium of the heart. The traumatic device 112 may be withdrawn through the lumen 100. S208. While the distal portion 18 of the medical device is in the left atrium of the heart, the distal portion 18 may be transitioned from the retracted configuration 42 to the expanded configuration 38. S210.

While in the expanded configuration 38, the distal portion 18 may be retracted from the left atrium to the right atrium of the heart through the orifice 114 that was created with the traumatic device 112. S212. When retracting the distal portion 18 in the expanded configuration 38, the cutting members 72 will come into contact with the tissue in the fossa ovalis to create a cruciform shaped 116 and valvular 118 shaped shunt in the tissue in the fossa ovalis. This cruciform shaped 116 and valvular 118 shaped shunt in the tissue in the fossa ovalis allows for blood flow from the left atrium to the right atrium of the heart which in turn will reduce the left atrial pressure in the heart. None of the tissue in the fossa ovalis is removed when the device is retracted from the left atrium to the right atrium of the heart through the orifice 114. In one embodiment, the diameter of the cruciform shaped 116 and valvular 118 shaped shunt may be between 5 millimeters and 20 millimeters. Creating a cruciform shaped 116 and valvular 118 shaped shunt in with this range of diameters will provide sufficient pressure relief within the heart while also inhibiting tissue healing so that the newly created cruciform shaped 116 and valvular 118 shaped shunt will not close once it has been created. The cruciform shaped 116 and valvular 118 shaped shunt will allow tissue to continuously move with the pressure changes in the heart so that the tissue will be less likely to heal and close the cruciform shaped 116 and valvular 118 shaped shunt which is unlike a circular disc shaped shunt where the edge of the punctured tissue is rigidly within the fossa ovalis tissue and therefore more likely to heal and close the shunt. Once the distal portion 18 of the medical device 10 is in the right atrium of the heart in the expanded configuration 38, the distal portion 18 may be transitioned from the expanded configuration 38 into the retracted configuration 42. S214. The transitioning of the distal portion 18 may occur in the right atrium of the heart. The medical device 10 may be withdrawn from the body of the patient. S216. These steps are shown in more detail in FIG. 6 with how the medical device 10 is moved, positioned, and removed from the heart of the patient.

Figure 6:
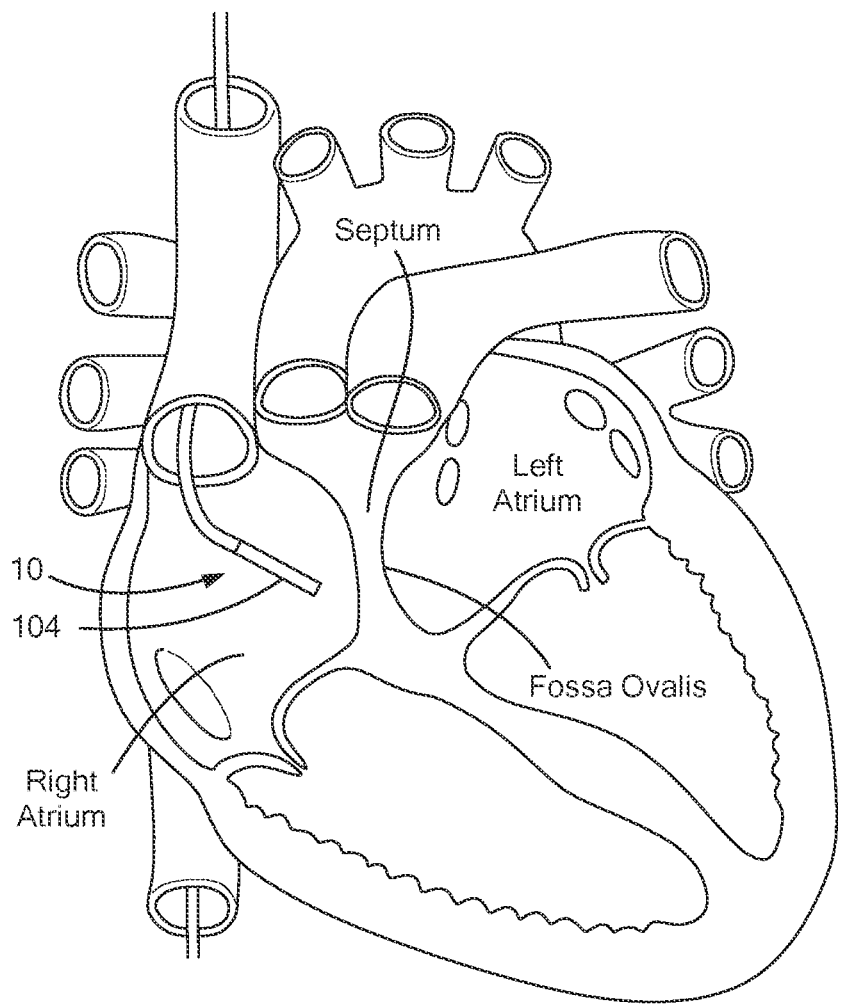
FIGS. 6A-6G are views of the medical device shown in FIG. 1 being inserted into the septum of the heart.
Figure 6:
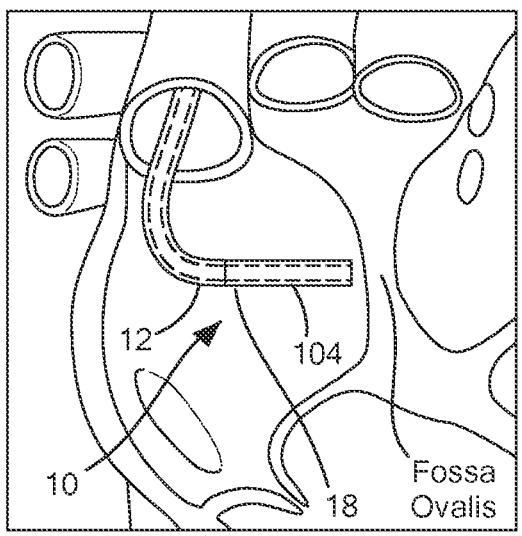
Figure 6:
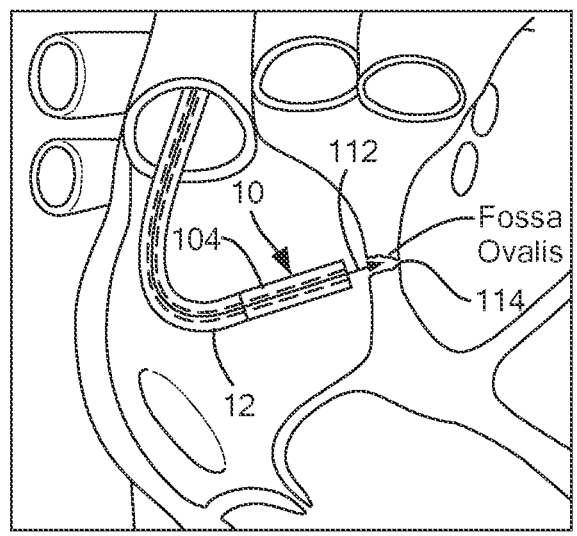
Figure 6:
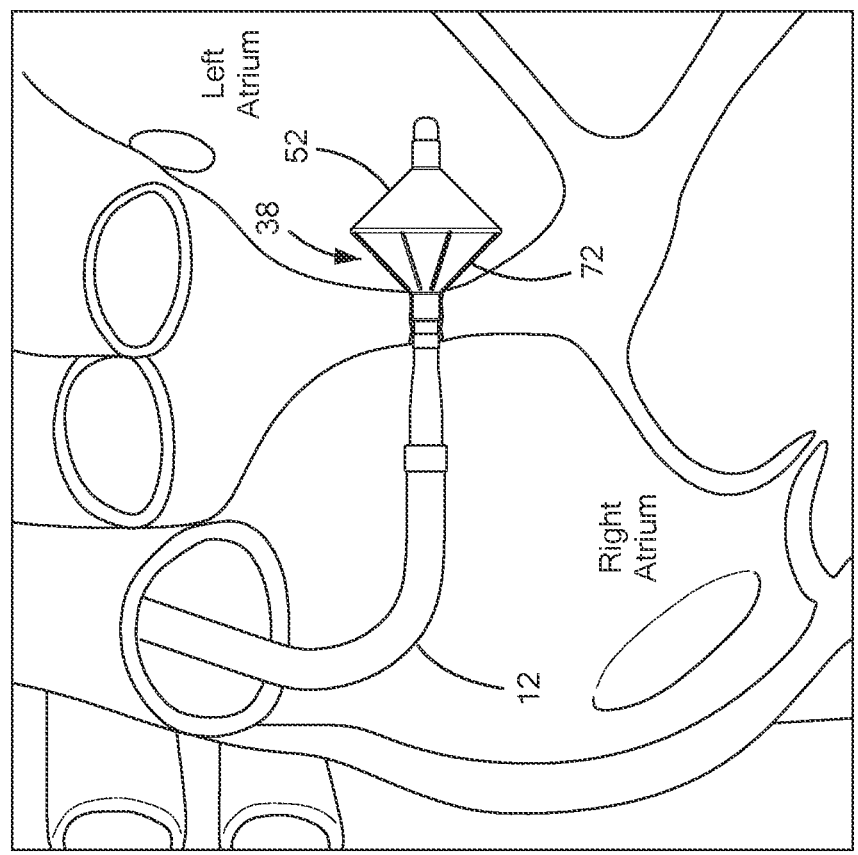
Figure 6:
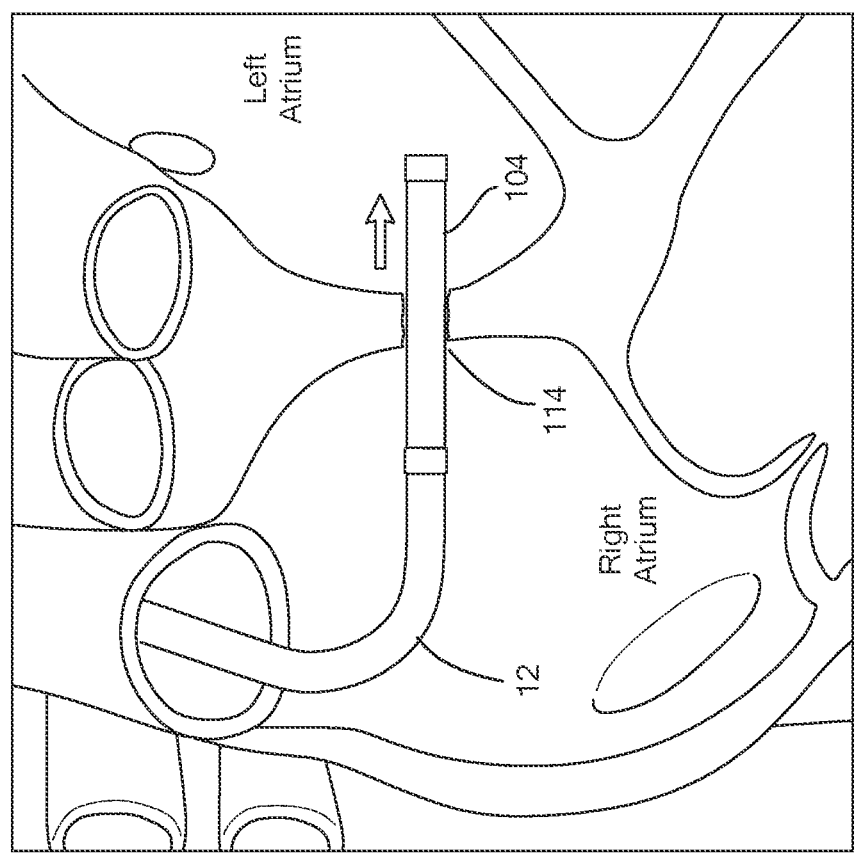
Figure 6:
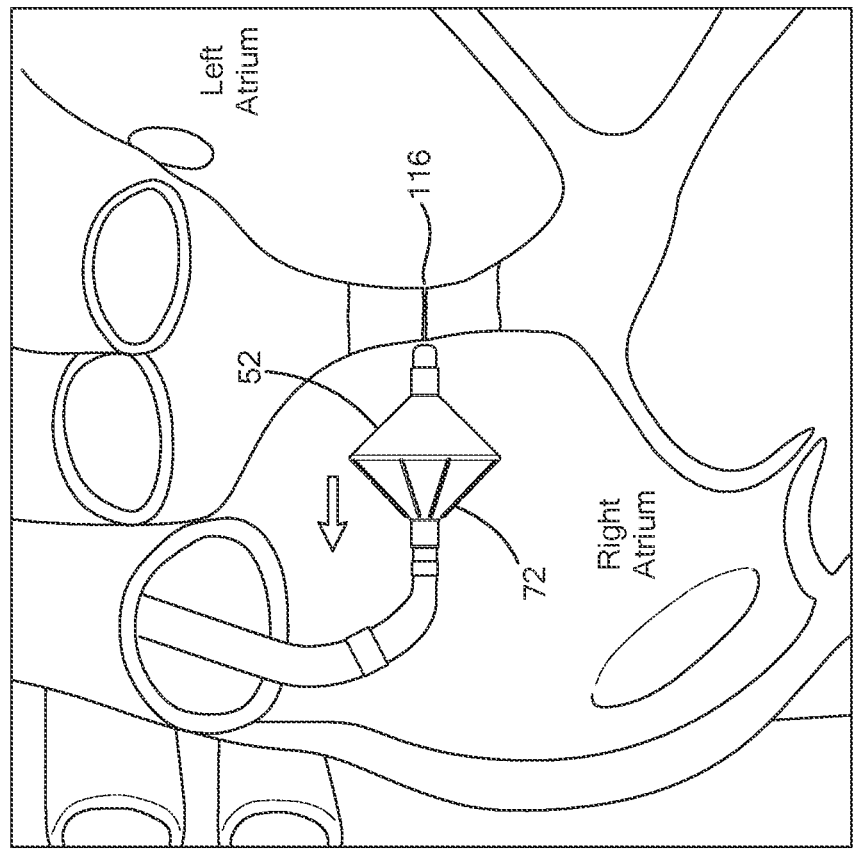
Figure 6:
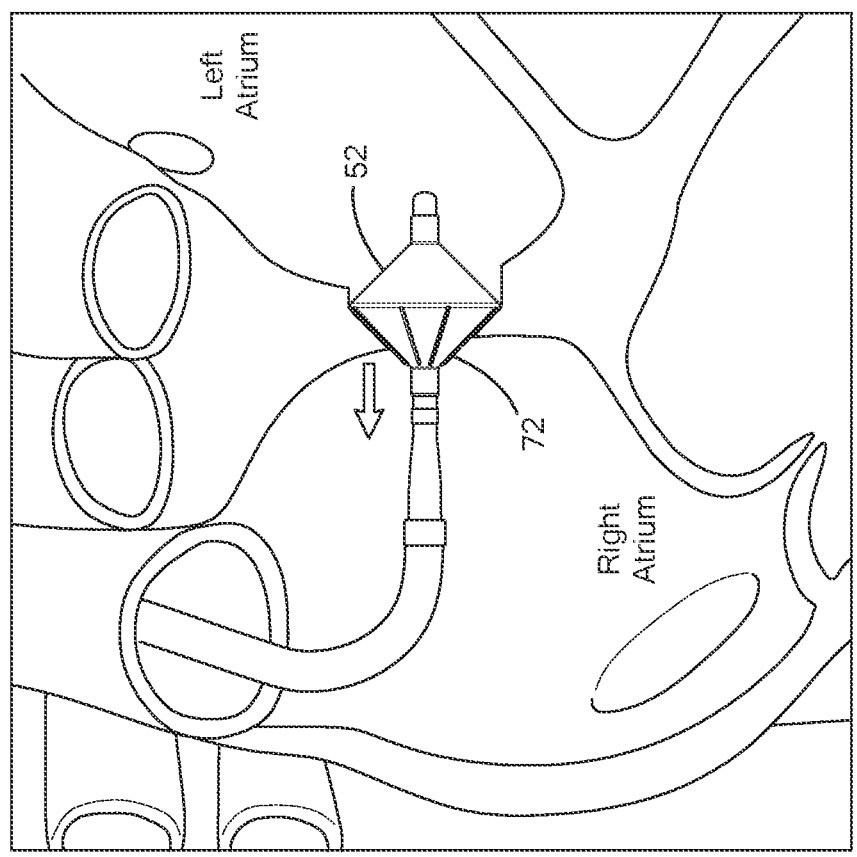

In FIG. 6, the medical device 10 is shown as positioned in the right atrium, the left atrium and the fossa ovalis of the patient's heart (FIGS. 6A-G). Before the medical device 10 is introduced into the patient's vasculature, the distal portion 18 may be in the retracted configuration 42 and then inserted into the vasculature of the body to create a smooth transition into the vasculature (FIG. 6A). The sheath 104 would cover the distal portion 18 so that the distal portion 18 can be easily maneuvered through the vessels in the body. The medical device 10 and the catheter body 12 may be flexible to allow for easy movement though the vasculature. Additionally, the catheter body 12 may include the actuator 24 with a deflection component or other component to allow the medical device 10 to curve and move through the vasculature. The medical device 10 may be moved through the patient's vasculature, which may include the superior vena cava, the inferior vena cava, or any other portion of the vasculature, and positioned in the right atrium of the heart (FIGS. 6A-6G).

Once the distal portion 18 of the medical device 10 is disposed proximate the fossa ovalis, the traumatic device 112 may be introduced into the lumen 100 and advanced through the lumen 100 into the distal portion 18 of the medical device 10. (FIGS. 6B-6C). The traumatic device 112 may travel through the lumen 100 and exit at the aperture 110 of the sheath 104 so that the traumatic device 112 may be used to puncture the fossa ovalis to create an orifice 114. Once the traumatic device 112 has created the orifice 114 in the tissue, the traumatic device 112 may be withdrawn from the lumen 100. The distal end 108 of the sheath 104 may be inserted into the orifice 114 and the medical device 10 may be advanced through the orifice 114 from the right atrium to the left atrium of the heart. The distal portion 18 of the medical device 10 in the retracted configuration 42 may be advanced through the orifice 114 so that the distal portion 18 of the medical device 10 is within the left atrium of the heart.

Once the distal portion 18 of the medical device 10 is in the left atrium of the heart, the distal portion 18 may be transitioned from the retracted configuration 42 into the expanded configuration 38. In transitioning between the retracted configuration 42 to the expanded configuration 38, the sheath 104 may be removed from the distal portion 18 to reveal the expandable element 52. Once the sheath 104 is removed, the expandable element 52 may be expanded so that the plurality of cutting members 72 that are disposed on the exterior surface 76 of the expandable element 52 and are arranged in a cruciform configuration. Additionally, in one embodiment, the expandable element 52 may be a balloon with a conical shape. Once the distal portion 18 is in the fully expanded configuration in the left atrium of the heart, the distal portion 18 of the medical device may be withdrawn, moved, and/or retracted from the left atrium of the heart into the right atrium of the heart through the fossa ovalis. Moving the distal portion through the fossa ovalis in this expanded configuration 38 will create the cruciform shape 116 and valvular 118 shunt in the tissue of the fossa ovalis. The cruciform shape 116 and valvular 118 shunt created in the tissue will be larger than the initial orifice 114 that was created when the traumatic device 112 was originally advanced through the fossa ovalis from the right atrium into the left atrium and then the distal portion 18 was advanced through this orifice 114 in the retracted configuration 42. FIG. 6E-6F.

Once the cruciform shape 116 and valvular 118 shunt has been created in the tissue of the fossa ovalis and the distal portion 18 in the expanded configuration 38 is completely in the right atrium of the heart, the distal portion may be transitioned into the retracted configuration 42 with the sheath 104 so that the medical device 10 may be removed from the body of the patient. The medical device 10 may also be used in any portion of a patient's vasculature and is not limited to the heart. How the medical device 10 is inserted and maneuvered throughout the body will depend upon the anatomical structure of the patient as well as the portion of the body that the medical device is being maneuvered within.

Figure 7:
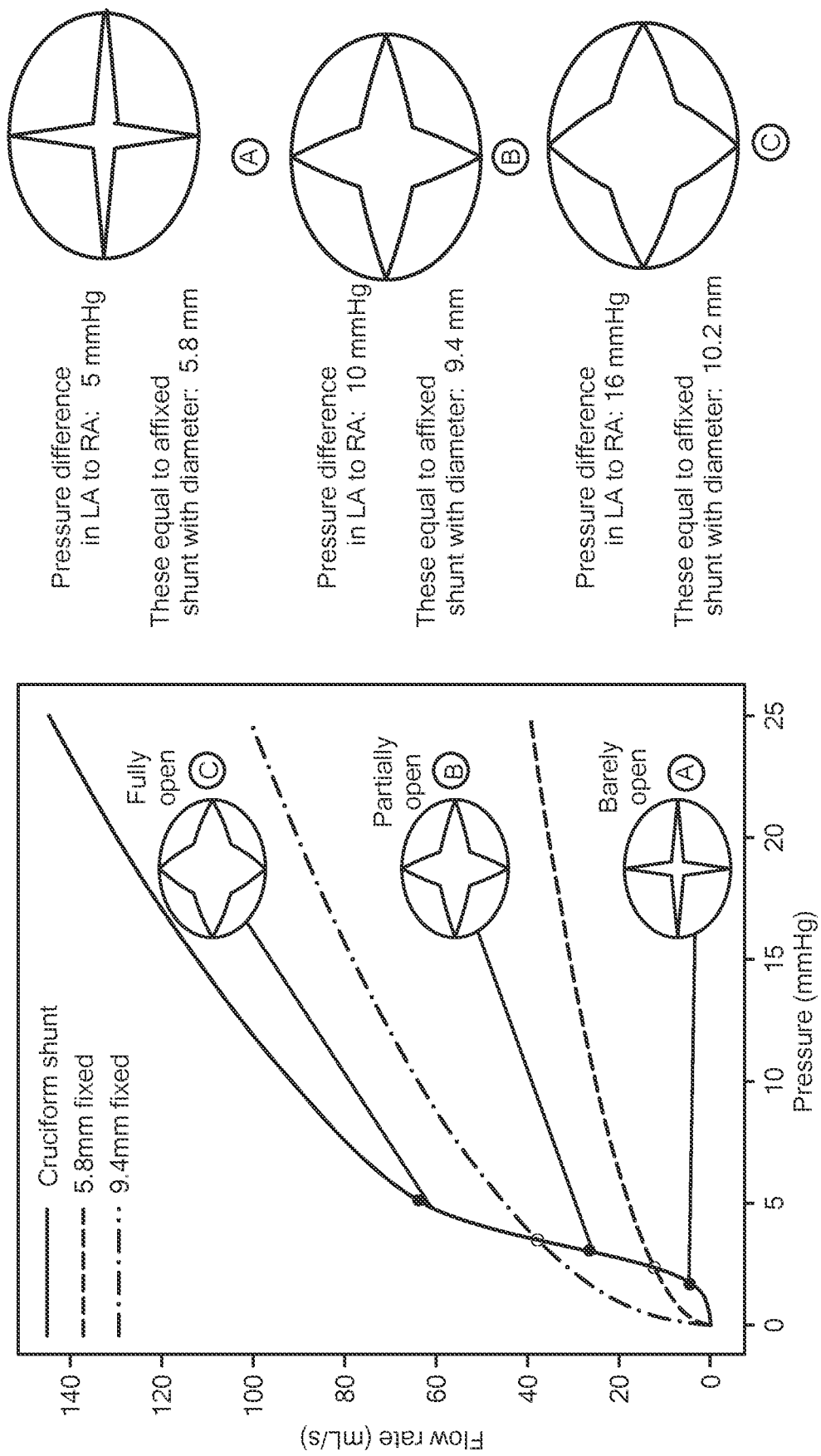
FIG. 7 are various schematics of the shunt at different pressures of the left atrium to the right atrium and the correlation of the blood flow rate to the pressure difference from the left to right atrium of the heart.

Now referring to FIG. 7, the cruciform shape 116 and valvular 118 shunt that is created in the tissue of the fossa ovalis can be self-regulated by pressure differences between the right atrium and the left atrium of the heart. The shape of the valvular 118 shunt that is created in the fossa ovalis of the heart can have a significant impact on the pressure within the heart and the flow of blood within the heart. As shown in FIG. 7, the valvular shunt that may be created by the medical device 10 may be a variety of different shapes and sizes and the shape and size of this valvular shunt can create significant pressure differences which can prevent the valvular shunt from healing. Preventing the valvular shunt from healing can allow the valvular shunt to remain intact and assist in changing the pressure and blood flow within the body. For example, as shown in FIG. 7, there are three different valvular shunts shown as A, B and C that have been created in the fossa ovalis of the heart. Valvular shunt C has the largest opening and generally has a total surface area of around 81.7 mm$^2$ and equal to a diameter of 10.2 mm. Valvular shunt B has is partially open and generally has a total surface area of around 69.4 mm$^2$ and equal to a diameter of 9.4 mm. Valvular shunt A has the smallest opening and generally has a total surface area of around 26.4 mm$^2$ and equal to a diameter of 5.8 mm. Valvular shunts B and A generally have a cruciform shape. FIG. 7 shows the flow rate from the left to right atrium of the heart on the y-axis as well as the pressure on the x-axis and how the different valvular shunts in the fossa ovalis of the heart can impact the flow of blood and the pressure within the right and left atrium of the heart. The flow rates can be self-regulated due to the pressure differences between the right atrium and the left atrium. For example, the changes in flow rate for the valvular shunt A or valvular shunt B, which have the cruciform configuration, show that flow rate is more efficiently regulated and maintained while also maintaining a smaller pressure difference between the left atrium and the right atrium of the heart. Additionally, the cruciform shape shown in valvular shunt B and valvular shunt A maintain minimal inter-atrial pressures of >2 mmHg which offers greater protection against retrograde flow as well of the blood in the heart. When the valvular shunt is fully open as shown in valvular shunt A, there is less control over the flow rate as well as the pressure which are significantly higher than when using the valvular shunt B and the valvular shunt A.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
an elongate body having a proximal portion, a distal portion, and defining a lumen therethrough;
an expandable element being coupled to the distal portion of the elongate body, the expandable element having an inner surface and an outer surface opposite the inner surface, the expandable element defining a proximal portion of the outer surface, a distal portion of the outer surface opposite the proximal portion of the outer surface and an intermediate portion of the outer surface disposed between the proximal portion of the outer surface and the distal portion of the outer surface; and
a plurality of cutting members, each cutting member being coupled with the outer surface of the expandable element, each cutting member having a proximal end and a distal end opposite the proximal end, the proximal end being proximate to the proximal portion of the outer surface and the distal end being proximate to the intermediate portion of the outer surface, the proximal portion of the outer surface having a first diameter, the distal portion of the outer surface having a second diameter, and the intermediate portion of the outer surface having a third diameter, the third diameter being larger than the first diameter and the second diameter.

2. The medical device of claim 1, wherein the expandable element is a conical shaped balloon.

3. The medical device of claim 1, where each cutting member further includes a plurality of segmented portions, each segmented portion being separated from an adjacent segmented portion by a slot.

4. The medical device of claim 3, wherein each segmented portion from the plurality of segmented portions includes a cutting element.

5. The medical device of claim 4, wherein each cutting member has three segmented portions and two slots, each segmented portion being separated from the adjacent segmented portion by one slot.

6. The medical device of claim 5, wherein the plurality of cutting members comprises four cutting members.

7. The medical device of claim 6, wherein each cutting member of the four cutting members comprises three segmented portions, each segmented portion having a cutting element.

8. The medical device of claim 7, wherein each cutting element extends away from the outer surface of the expandable element.

9. The medical device of claim 1, further comprising a sheath, the expandable element being transitional between a retracted configuration and an expanded configuration, when the expandable element is in the retracted configuration, the sheath is disposed over at least a portion of the expandable element.

10. The medical device of claim 9, wherein when the expandable element is in the expanded configuration, the sheath is not disclosed over the expandable element.

11. The medical device of claim 1, wherein the first diameter is the same as the second diameter.

12. A medical device comprising:
an elongate body having a proximal portion, a distal portion, and defining a lumen therethrough;
a balloon being coupled to the distal portion of the elongate body, the balloon having an inner surface and an outer surface opposite the inner surface, the balloon having a conical shape and defining a proximal portion of the outer surface, a distal portion of the outer surface opposite the proximal portion of the outer surface and an intermediate portion of the outer surface disposed between the proximal portion of the outer surface and the distal portion of the outer surface;
a plurality of cutting members, each cutting member being coupled with the outer surface of the balloon, each cutting member having a proximal end and a distal end opposite the proximal end, the proximal end being proximate to the proximal portion of the outer surface and the distal end being proximate to the intermediate portion of the outer surface, the proximal portion of the outer surface having a first diameter, the distal portion of the outer surface having a second diameter, and the intermediate portion of the outer surface having a third diameter, the third diameter being larger than the first diameter and the second diameter; and
a plurality of segmented portions defined between the proximal end and the distal end of the cutting members, each segmented portion being separated from an adjacent segmented portion by a slot.

13. The medical device of claim 12, wherein each segmented portion from the plurality of segmented portions includes at least one cutting element.

14. The medical device of claim 13, wherein each cutting member has three segmented portions and two slots, each segmented portion being separated from the adjacent segmented portion by one slot.

15. The medical device of claim 12, wherein the plurality of cutting members comprises four cutting members.

16. The medical device of claim 15, wherein each cutting member of the four cutting members comprises three segmented portions, each segmented portion having a cutting element.

17. A method for delivering a medical device, comprising:
positioning a medical device proximate the fossa ovalis of a patient's heart in the right atrium, the medical device including:
an elongate body having a proximal portion, a distal portion, and defining a lumen therethrough;
an expandable element being coupled to the distal portion of the elongate body, the expandable element having an inner surface and an outer surface opposite the inner surface, the expandable element defining a proximal portion of the outer surface, a distal portion of the outer surface opposite the proximal portion of the outer surface and an intermediate portion of the outer surface disposed between the proximal portion of the outer surface and the distal portion of the outer surface; and
a plurality of cutting members, each cutting member being coupled with the outer surface of the expandable element, each cutting member having a proximal end and a distal end opposite the proximal end, the proximal end being proximate to the proximal portion of the outer surface and the distal end being proximate to the intermediate portion of the outer surface, the proximal portion of the outer surface having a first diameter, the distal portion of the outer surface having a second diameter, and the intermediate portion of the outer surface having a third diameter, the third diameter being larger than the first diameter and the second diameter,
advancing a traumatic device through the lumen of the medical device;
puncturing the fossa ovalis with the traumatic device to create an orifice;
withdrawing the traumatic device through the lumen;
advancing the medical device through the orifice from the right atrium of the heart to the left atrium of the heart until the distal portion of the medical device is in the left atrium;
transitioning the distal portion of the medical device into an expanded configuration;
retracting the distal portion of the medical device in the expanded configuration from the left atrium to the right atrium of the heart;
transitioning the distal portion from the expanded configuration to a retracted configuration; and
withdrawing the medical device from the body.

18. The method of claim 17, where the traumatic device is a puncturing device or a guidewire.

19. The method of claim 17, wherein the plurality of cutting members is four cutting members.

* * * * *